US006849183B2

(12) United States Patent
Gorsuch et al.

(10) Patent No.: US 6,849,183 B2
(45) Date of Patent: Feb. 1, 2005

(54) METHOD AND APPARATUS FOR THERAPEUTIC APHERESIS

(75) Inventors: Reynolds G. Gorsuch, Yountville, CA (US); Tommy Cooper, Friendswood, TX (US)

(73) Assignee: Transvivo, Inc., Napa, CA (US)

( * ) Notice: Subject to any disclaimer, the term of this patent is extended or adjusted under 35 U.S.C. 154(b) by 151 days.

(21) Appl. No.: 10/219,082

(22) Filed: Aug. 13, 2002

(65) Prior Publication Data

US 2004/0034317 A1 Feb. 19, 2004

(51) Int. Cl.$^7$ .................... B01D 61/00; C02F 1/44
(52) U.S. Cl. ............ 210/646; 210/645; 210/321.71; 210/500.23; 604/5.01; 604/6.01; 604/500.23
(58) Field of Search .................... 210/645, 646, 210/650, 321.69, 321.71, 321.88, 321.79, 500.23; 604/5.01, 6.01, 6.09

(56) References Cited

U.S. PATENT DOCUMENTS

| | | | |
|---|---|---|---|
| 4,235,231 A | * 11/1980 | Schindler et al. | 604/6.09 |
| 4,832,034 A | 5/1989 | Pizziconi et al. | 128/632 |
| 4,950,224 A | 8/1990 | Gorsuch et al. | 604/4 |
| 5,145,583 A | 9/1992 | Angleraud et al. | 210/646 |
| 5,151,082 A | 9/1992 | Gorsuch et al. | 604/4 |
| 5,152,743 A | 10/1992 | Gorsuch et al. | 604/4 |
| 5,224,926 A | 7/1993 | Gorsuch et al. | 604/4 |
| 5,605,627 A | 2/1997 | Carlsen et al. | 210/321 |
| 5,735,809 A | 4/1998 | Gorsuch | 604/4 |
| 5,968,004 A | 10/1999 | Gorsuch | 604/4 |
| 5,980,478 A | 11/1999 | Gorsuch et al. | 604/4 |
| 5,980,481 A | 11/1999 | Gorsuch | 604/28 |

FOREIGN PATENT DOCUMENTS

| | | |
|---|---|---|
| EP | 0 882 494 A1 | 12/1998 |
| FR | 2566003 | 12/1985 |
| JP | 932031 | 12/1997 |

OTHER PUBLICATIONS

A. Sueoka, Present Status of Apheresis Technologies: Part 2. Membrane Plasma Fractionator, *Therapeutic Apheresis*, vol. 1, No. 2, pp. 135–146, May 1997.

Ronco, et al. A Novel approach to the Treatment of Chronic Fluid Overload with a New Plasma Separation Device, *Cardiology 2001*; 96:135–146, Jan. 2002.

Handley, et al., Intravenous Catheter for Intracorporeal Plasma Filtration, *Blood Purification 2000*, 20:61–69, Jan. 24, 2002.

* cited by examiner

*Primary Examiner*—W. L. Walker
*Assistant Examiner*—K S Menon
(74) *Attorney, Agent, or Firm*—Knobbe, Martens, Olson & Bear, LLP

(57) ABSTRACT

A method for carrying out therapeutic apheresis comprises separating plasma from whole blood in-vivo and removing selected disease-related components from the separated plasma. Apparatus for carrying out therapeutic apheresis includes a filter device for being implanted in a blood vessel for carrying out in-vivo plasma separation having one or more elongated hollow tubes and a plurality of elongated hollow microporous fibers capable of separating plasma from whole blood at pressure and blood flow within a patient's vein, a multiple lumen catheter secured to the proximal end of the filter device having one or more lumens in fluid communication with the interior of said one or more hollow tubes and a plasma return lumen, and therapeutic apheresis apparatus for removing and/or separating selected disease-related components from the separated plasma and means for directing plasma between said catheter and the selective component removal apparatus.

25 Claims, 4 Drawing Sheets

METHOD AND APPARATUS FOR THERAPEUTIC APHERESIS

BACKGROUND OF THE INVENTION

In the field of medicine, the term "therapeutic apheresis" refers to techniques for treating diseases using the patient's blood. Current medical practice extracts whole blood from the patient and, as a first stage, separates the plasma from the blood ex-vivo by centrifugal or membrane separation, and in a second stage treats the separated plasma by various techniques. The treated plasma and blood are recombined ex-vivo and returned to the patient. In the simplest procedure the separated plasma including the pathogenic macromolecules is discarded and substitution fluids such as fresh frozen plasma and albumen solution are re-infused to the patient.

In all of the aforesaid and currently practiced therapeutic apheresis procedures, whole blood must be removed from the body and processed in two ex-vivo stages. However, removal and treatment of whole blood has major disadvantages. Whole blood removal results in the necessity to heparinize or anticoagulate the patient to minimize clotting in the ex-vivo circuit and apparatus. Such treatment is counter-indicated in most surgical patients and deleterious to others due to consequential damage to blood components and the removal of vital blood components unrelated to the therapy. Removing and treating whole blood ex-vivo dictates that the procedure be a "batch" or intermittent process with attendant loss of efficiency and confinement of the patient to a clinical setting where support systems and machinery are available. Removal of whole blood also exposes the patient to contamination by viral and/or bacterial infection from nosocomial sources, and removal of erythrocytes, platelets and other large cellular blood components exposes them to risk of damage due to mechanical and chemical exposure to non-biocompatible surfaces of ex-vivo apparatus.

SUMMARY OF THE INVENTION

The present invention relates to methods and apparatus for carrying Out therapeutic apheresis. In the present invention, plasma, not whole blood, is removed from the patient in a first stage of therapeutic apheresis. Plasma separation is performed in-vivo by a plasma separation filter placed in an appropriate vein and the separated plasma is pumped to a therapeutic apheresis selective component removal system for separating and removing selected disease-related plasma components or plasma containing such components such as toxins, antibodies, proteins, bacteria, and/or viruses. After the appropriate disease-related plasma component is extracted by the therapeutic apheresis apparatus, the processed plasma, and if desired fresh plasma, is pumped to the patient.

In a preferred embodiment, a system used for carrying out therapeutic apheresis comprises apparatus including a filter device for being implanted in a blood vessel for in-vivo plasma separation incorporating a plurality of elongated microporous hollow fibers having an asymmetrical fiber wall morphology in which the inner wall surface along the interior fiber lumen has a lower mass density and the fiber wall adjacent to the outer wall surface has a higher mass density. A preferred filter device comprises one or more elongated hollow tubes to which opposite ends of each of the fibers are secured so that the interior of the one or more hollow tubes communicates with the interior of each of the elongated hollow fibers. The system includes a triple lumen catheter, secured to a proximal end of the one or more hollow tubes for directing blood plasma passing through the fiber walls and into the fiber lumen to therapeutic apheresis selective component removal apparatus. The system also includes fluid control piping and cooperating pumps for directing plasma between system components. The system includes backflush components comprising piping, backflush pump and source of backflush fluid selectively directed to the filter device for a duration and flow rate sufficient to substantially cleanse filter pores. In a preferred embodiment, operation of the system is controlled by a microprocessor/controller.

DETAILED DESCRIPTION OF THE PREFERRED EMBODIMENTS

Figure 1:
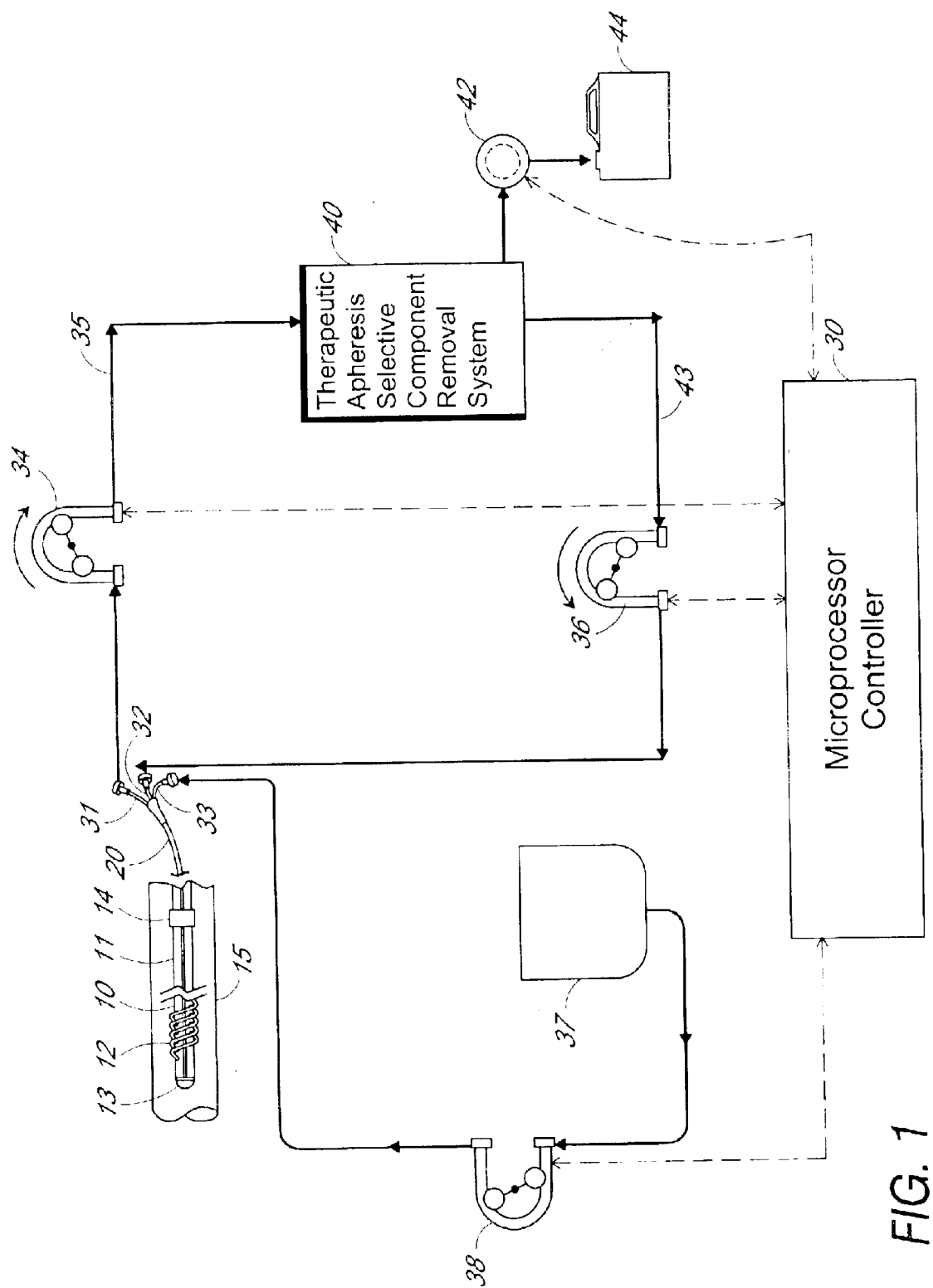
FIG. 1 is a schematic illustration of a preferred embodiment of apparatus for carrying out therapeutic apheresis.
Figure 4:
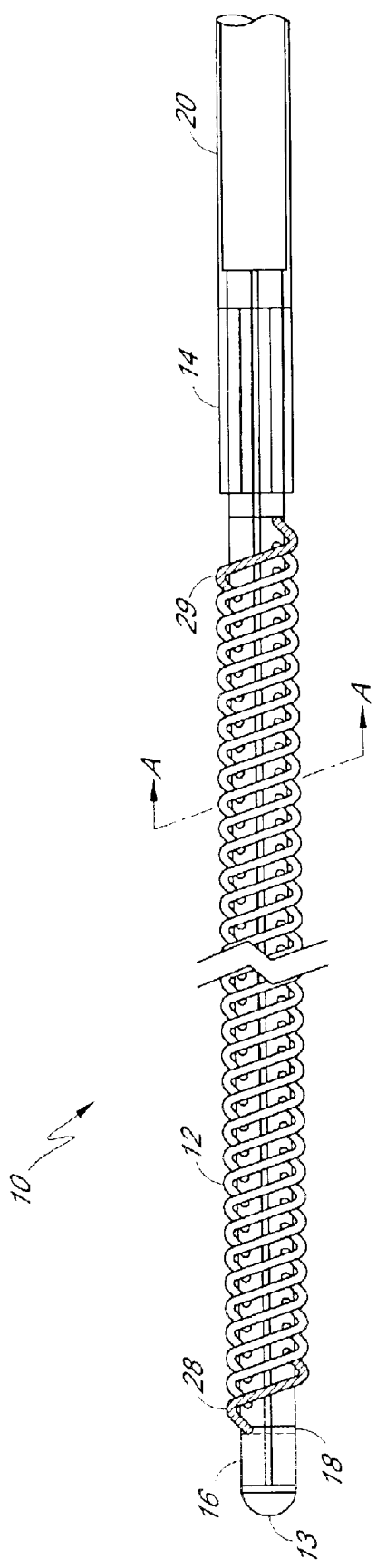
FIG. 4 is a top view of a preferred embodiment of a filter device shown in FIG. 1 for separating plasma from blood in-vivo having a pair of elongated substantially parallel hollow tubes joined together along their length, showing distal and proximal end segments.
Figure 6:
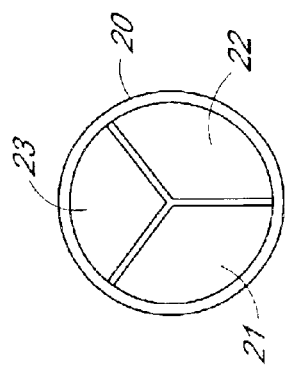
FIG. 6 is a sectional view of a triple lumen catheter of the apparatus shown in FIG. 1 illustrating the catheter interior.
Figure 5:
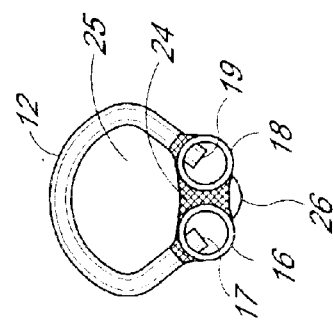
FIG. 5 is an enlarged sectional view of the filter device of FIG. 3 along the lines A—A showing a single elongated hollow fiber secured to the hollow tubes.

The preferred embodiment of an apparatus for carrying out therapeutic apheresis according to the invention schematically illustrated in FIG. 1 includes a filter device 10, a triple lumen catheter 20, a therapeutic apheresis selective component removal apparatus 40, a fluid control assembly including tubing and pumps, and a microprocessor/controller 30. The filter device 10, which will be described in more detail hereinafter, is implantable in the vasculature of a patient or animal in which in-vivo plasma separation is to be carried out. Veins suitable for implanting the filter include the superior or inferior vena cava or the subclavian vein. In the drawing, the filter device 10 is shown implanted in the inferior vena cava 15. A triple lumen catheter 20 is secured to the proximal end 11 of the filter with header 14. Triple lumen catheter 20 is in fluid communication with the interior of the filter device with the three catheter lumens connected to tubing for directing outgoing plasma, return plasma, and backflush fluid. Referring also to FIGS. 4–6, plasma separated from whole blood through the microporous fibers 12 of the filter device are directed through access lumen 21 and first tubing 31 to selective component apparatus 40. Plasma is separated from whole blood within the blood vessel in which the filter device is inserted using trans-membrane pressure (TMP) supplied by access pump or first pump 34, a positive displacement volumetric pump that operates to regulate pressure and control trans-membrane pressure and plasma volume removal rate.

Plasma from the filter device is pumped to the therapeutic apheresis selective component removal apparatus 40 for selectively removing disease-related components such as toxins, antibodies, proteins, pathogens including bacteria, virus, etc., and other disease-related substances desired to be removed. Plasma components and solutes removed from the treated plasma are directed to a container 44. An effluent pump 42 is optional and may be advantageously used for assisting in controlling the rate of disease components removed by providing controlled trans-membrane pressure across filter membranes of the selective component removal apparatus. Plasma is returned to the patient via tubing 43 at a rate controlled by pump 36. The tubing 43 is in fluid communication with plasma return tube 32 which is connected to plasma return lumen 22 of triple lumen catheter 20 (FIG. 5).

Examples of selective component removal apparatus used for therapeutic apheresis include plasma exchange components, centrifugal or membrane-separation filters, such as disclosed in U.S. Pat. No. 5,605,627, cascade or multiple filtration membranes and columns, cartridges having components for absorbing (adsorbing) specific disease-related components, and activated charcoal cartridges. Other examples of useful selective component removal components include specialized columns utilizing materials such as cross-linked polyvinyl alcohol gel beads or microporous cellulose beads for removing specific amino acid ligands and antibodies. Further examples of selective component removal apparatus are chemical process systems for specialized uses such as heparin precipitation, plasma cyrofiltration, and salt-amino acid co-precipitation, and the like. Chemical process apparatus for effectively neutralizing disease related components in the plasma may also be used. These and other selective component removal apparatus and technologies are described in *Therapeutic Apheresis*, Official Journal of the International Society for Apheresis, Vol. 1–6, Blackwell Science Inc., "Present Status of Apherisis Technologies", e.g. Vol. 1, No. 2, May, 1997, pp. 135–146 the descriptions of which are incorporated herein by reference. Combinations of two or more of any of the aforesaid apparatus may also be used.

Figure 2:
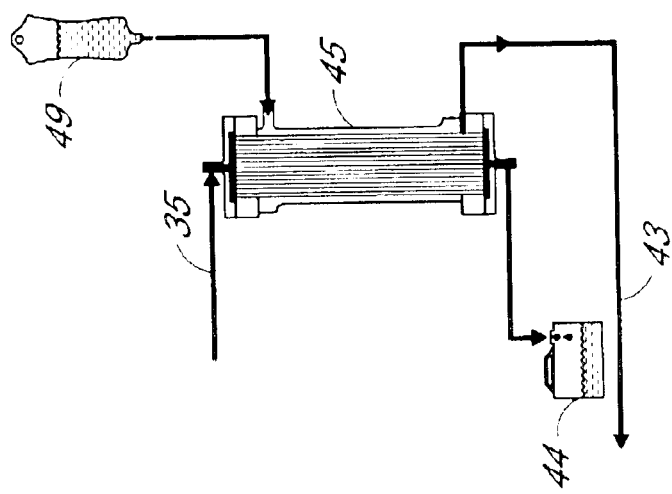
FIG. 2 schematically illustrates one embodiment of therapeutic apheresis apparatus using plasma exchange.

FIG. 2 illustrates a plasma exchange apparatus 45 for separating plasma components and for delivering fresh plasma from supply source 49. The plasma exchange rate may be selected as a function of the plasma removal rate by proportioning the rate of operation of access pump 34 to effluent pump 42, as shown in FIG. 1.

Figure 3:
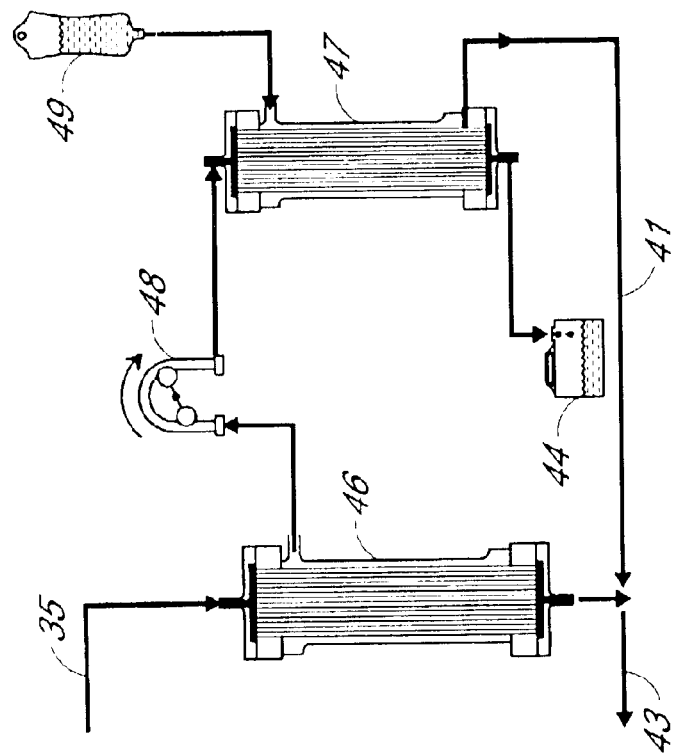
FIG. 3 schematically illustrates a therapeutic apheresis apparatus embodiment using double, cascade filtration.

FIG. 3 schematically illustrates an example of selective component removal apparatus showing a cascade filter comprising a first stage filter 46 and a second stage filter 47. A pump 48 is used for directing fluid plasma from the first stage filter to the second stage filter. A source of make-up plasma liquid 49 may be used, if desired, for introducing substitution fluids such as fresh plasma which is combined with the treated plasma to be returned to the patient via tubing 41 and 43. Container 44 receives and collects discarded plasma fluid containing disease-related components, such as toxins, etc. as previously described. In a single stage treatment apparatus, the use of a make-up plasma liquid is also optional as is effluent pump 42 shown in FIG. 1 and cooperating with selective component removal apparatus 40 for directing fluid and components to be discarded. Again, following treatment in selective component removal apparatus 40, plasma is returned to the patient via piping 43 and positive displacement pump 36 to plasma return tube 32 which is in fluid communication with plasma return lumen 22 of triple lumen catheter 20 (see FIG. 6).

An apparatus using cartridges or columns for absorbing or adsorbing disease-related components may also be used for treating separated plasma. Such apparatus may be configured like or similar to that illustrated in FIGS. 2 and 3 in which the columns shown incorporate absorbing or adsorbing filters comprising materials capable of absorbing selected disease-related components such as discussed herein. Again, such an apparatus may include a source of fresh plasma to be directed to the patient, if desired.

The preferred apparatus shown in FIG. 1 includes backflush fluid reservoir 37, backflush pump 38 and backflush tube 33 communicating with a backflush lumen of the triple lumen catheter. Such backflush components and method are disclosed in U.S. Pat. No. 6,659,973 to Gorsuch, et al., the descriptions of which is incorporated herein by reference. Backflush pump 38 is selectively and periodically operated to provide backflush fluid flow for substantially cleansing the pores of the fiber membrane of the filter device. Such a backflush cycle is preferably operated at high trans-membrane pressure and low volume and at relatively short injection times for backflushing whereby the membrane pores are temporarily expanded and flushed to dislodge adhered proteins, thereby restoring pore integrity and density of the virtual filter area for improved performance after each backflush cycle.

Fluid control of plasma within the apparatus may be controlled using a microprocessor/controller operatively communicating with the positive displacement volumetric pumps for controlling trans-membrane pressure in the filter device and selective component removal apparatus, plasma removal rate, plasma return rate and backflush pressure and rate. Such fluid control and management may be selected, tailored or designed for slow, continuous acute fluid removal. For example, operation of the system may be used for controlling plasma extraction rate from blood to achieve removal of 1–2 L of plasma water over a 24-hour period. The fluid control assembly may also include volume sensors, pressure sensors, blood leak detectors and air detectors connected to the piping and reservoirs as desired. As illustrated in FIG. 1, the microprocessor/controller 30 is operatively connected to the pumps. Similarly, the microprocessor/controller operates for controlling backflush pump 38 and plasma is returned at a selected rate by controlling pump 36. The microprocessor/controller may be programmed for flow rates designed to a the prescribed patient therapy.

In a preferred embodiment of the filter device 10 illustrated in FIGS. 1, 4 and 5, a pair of elongated hollow tubes are joined side-by-side lengthwise to form the core of the filter device. The two elongated hollow core tubes 16 and 18 terminate at a distal end with a distal end plug or cap 13 formed of a material that seals the open tube ends. The tubes and end cap may be made of any suitable biocompatible material, for example, medical grade extruded urethane tubes. Other biocompatible materials include synthetic rubbers, polycarbonate, polyethylene, polypropylene, nylon, etc. The elongated hollow tubes may be secured together using suitable bonding material 24, adhesive composition, etc., for example, a UV curable adhesive applied along the length between the two tubes. The length and diameter of the filter device may be selected to accommodate the vessel or vein in which it is to be implanted. Accordingly, the diameter and length of the one or more elongated hollow tubes forming the central core of the filter device are selected. A suitable tube length is between about 15 cm and about 25 cm, and preferably between about 18 cm and about 22 cm. Where a pair of core tubes is used as shown in the preferred embodiment, an outer diameter of each tube of between about 1 mm and about 3 mm is suitable. A detectable marker component 26, e.g., a radio opaque material, may also be bonded to the device, for example, in bonding material 24 extending along the length of the tubes to assist in implanting and/or monitoring the device during insertion, use and removal.

Effective plasma separation is also a function of fiber length. Thus, the length of the individual hollow fibers is preferably less than about 5 mm and preferably between about 1 mm an about 4 mm. Moreover, fiber orientation relative to blood flow within the vessel is also of significant importance. Preferably, the fibers are aligned so that the longitudinal fiber axis is between about 45° and about 90° relative to the direction of blood flow. The filtration performance of a filter device to separate plasma from whole blood in vivo is also a function of the filter surface of the exposed fibers whereby consideration is given to use larger diameter fibers and to maximize the number of fibers. It is desirable to use as many individual fibers along the hollow core tubes of the filter device as is practical while maintaining separation of the individual fibers to provide for fluid flow therebetween, and to maximize the amount of outer fiber surface exposed to blood flowing along the length of the filter device. Moreover, the fibers are secured along the length of the hollow tubes in such a manner as to form a fluid flow space between the fibers and the tubes. The length of the filter device as well as the overall cross-sectional dimension are tailored or dictated by the blood vessel in which the device is to be used so as to avoid substantial interference with blood flow through the vessel while at the same time be efficient to achieve the intended flow rate of separated plasma.

Preferably, the ends of each of the fibers are offset longitudinally relative to one another. Referring to FIGS. 4 and 5, elongated hollow fiber 12 has a first end 17 secured in first elongated hollow tube 16 and second end 19 secured in second hollow tube 18. In the specific device illustrated, the longitudinal spacing between the first and second ends of each fiber is a three-hole or three-fiber offset, e.g., about 0.5 cm. However, with intervals between the adjacent fiber ends of between about 0.1 cm and about 1.0 cm, offsets between first and second fiber ends may be between about 0.3 cm and about 3.0 cm, by way of example. With such offsets between first and second fiber ends, a straight line extending between the ends of a fiber forms an acute angle with an elongated axis of either or both of the elongated hollow tubes, and whereby the fibers also extend lengthwise between their ends along an angle other than 90° relative to the axes of the elongated hollow tubes. The acute angle preferably is between about 45° and about 85°. However, other fiber angles including 90° are not precluded and may be used where desired. Such fiber angles provide desirable fiber orientation relative to blood flow as previously described. Other filter device embodiments which may be used are disclosed in copending application Ser. No. 09/981,783 filed Oct. 17, 2001, the descriptions of which are incorporated herein by reference.

Conventional hollow fibers or filter membranes such as those used in conventional dialysate filter devices are unable to successfully perform in-vivo, intravascular plasma separation, becoming clogged within a very short period of time, e.g., minutes, as proteinaceous materials, blood platelets, and other components rapidly occlude the membrane pores. Conventional dialysate filter membranes have little structural strength which, although acceptable in an encapsulated dialysate filter environment external to the body, are not suitable for intravascular use. Moreover, conventional dialysate hollow fiber membrane filters do not perform satisfactorily in-vivo because of the relatively high flow rate of blood at the exterior fiber surface and relatively low lumen pressure as compared to dialysate filter apparatus conditions in which plasma separation is carried out at relatively low flow rates and high trans-membrane pressures. For example, typical in-vivo blood flow within a vena cava is about 2.5 L per minute, while blood flow through typical dialysate filter apparatus is nearly stagnant, e.g., about 0.42 ml per minute per fiber. Intravascular trans-membrane pressure is typically about 50 mm Hg or less, as compared to 100–300 mm Hg used in extracorporeal dialysate filters.

Figure 7:
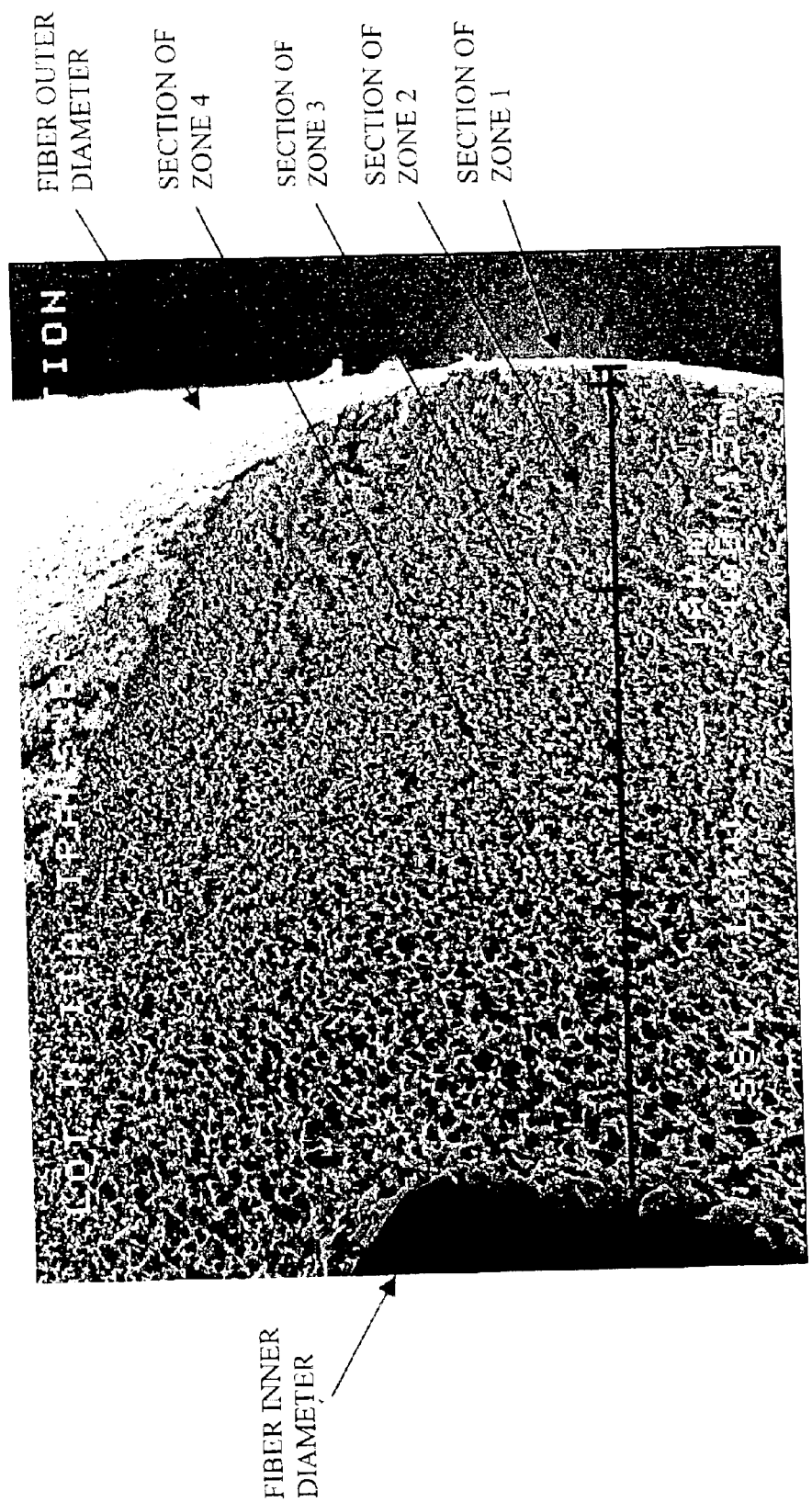
FIG. 7 is a scanning electron microscopy (SEM) image of a cross-section of a preferred elongated hollow fiber used in a filter device shown in FIG. 3 at 400 $\mu$m magnification.

The preferred elongated hollow microporous fibers used in the filter device described herein are the asymmetrical wall fibers disclosed in U.S. patent application Ser. No. 09/549,131 filed Apr. 13, 2000, the descriptions of which are incorporated herein by reference. The fiber wall structure of the elongated microporous fibers is asymmetrical between the inner wall surface extending along the interior fiber lumen and the outer fiber wall surface exposed to blood in the vessel in which the filter device is implanted. The fiber wall at or adjacent to the outer wall surface has a higher mass density than the mass density adjacent to or at the inner wall surface. The mass density is a function of the average nominal pore size. Such asymmetric fiber wall morphology is illustrated in FIG. 7 showing a scanning electron microscopy (SEM) image of a cross-section of the fiber at 400 $\mu$m magnification. It will be observed that the structure of the fiber from the outer surface to the lumen is a continuous change in mass density whereby the pore size gradually changes between these fiber wall surfaces. The fiber walls are also characterized by a substantially uniform wall thickness between the inner and outer wall surfaces and have substantially no macrovoids other than the pores, as shown. It is convenient to describe the continuum of different mass density as sections or zones of the wall area having an average nominal pore size or average pore diameter, each zone having a different average nominal pore size. Thus, the walls may be characterized by two or more zones, for example 2, 3, or 4 or more mass density zones. The hollow fiber shown in FIG. 7 is also shown and described in the aforesaid application Ser. No. 09/549,131.

The advantages which may be accrued by using the therapeutic apheresis methods and apparatus described above include elimination of the disadvantages of the removal of whole blood from the body and subsequent ex-vivo plasma separation as previously described. In-vivo plasma separation permits continuous real time therapy in most applications with resultant improvement in effectiveness, and in many applications would result in the ability to perform the therapy in a home setting or ambulatory mode which could be a major improvement in patient lifestyle as well as economy for the medical care system. Moreover, the use of the methods and apparatus described herein would increase the capacity of most caregiver organizations which are now limited by patient load capacity including the number of centrifuge machines available in the facility.

Examples of diseases and disorders for which therapeutic apheresis may be used and the pathogenic substances removed using the methods and apparatus of the invention include those listed in Exhibit 1, and described in *Therapeutic Apherisis*, Vol. 1, No. 2, 1997. The list is not intended to be exhaustive, and other diseases and substances may also be treated. Moreover, the methods and apparatus described herein may also be used in drug treatment, for example in drug overdose cases, where one or more toxic substances in the blood stream may be removed using the aforesaid methods and apparatus. These as well as others advantages will be evident to those skilled in the art.

What is claimed is:

1. A method of carrying out therapeutic apheresis comprising:

securing a triple lumen catheter having a filter device on the proximal end thereof in a blood vessel of a patient, said filter device capable of separating plasma from whole blood in-vivo at pressures and flow rates therein;

separating plasma from whole blood in-vivo and directing the separated plasma through a first lumen of said triple lumen catheter to a therapeutic apheresis selective component removal apparatus;

carrying out therapeutic apheresis by separating and removing and/or neutralizing selected disease-related components comprising toxins, antibodies, proteins, bacteria, viruses, and/or combinations of two or more thereof from the plasma, returning treated plasma to the patient via a second lumen of said triple lumen catheter; and selectively periodically backflushing said filter device via a third lumen of said triple lumen catheter.

2. The method of claim 1 wherein said therapeutic apheresis is carried out by plasma exchange wherein at least a portion of the separated plasma is replaced with fresh plasma.

3. The method of claim 1 wherein said therapeutic apheresis is carried out by cascade filtration.

4. The method of claim 3 including substituting fresh plasma for a portion of said separated plasma.

5. The method of claim 1 wherein said therapeutic apheresis is carried out by absorption.

6. The method of claim 5 comprising passing the separated plasma through an absorbent cartridge apparatus for absorbing disease-related components therefrom.

7. The method of claim 5 including substituting fresh plasma for a portion of said separated plasma.

8. The method of claim 1 wherein said therapeutic apheresis is carried out by exposing the separated plasma to one or more devices capable of removing a specific disease-related component from the separated plasma.

9. The method of claim 8 including substituting fresh plasma for a portion of said separated plasma.

10. The method of claim 1 wherein said therapeutic apheresis is carried out by directing the separated plasma through one or more chemical process systems for precipitating or neutralizing one or more disease-related components therein.

11. The method of claim 10 including substituting fresh plasma for a portion of said separated plasma.

12. A method of carrying out therapeutic apheresis comprising:

securing a triple lumen catheter having a filter device on the proximal end thereof in a blood vessel of a patient, said filter device capable of separating plasma from whole blood in-vivo at pressures and flow rates in said blood vessel and comprising a plurality of elongated hollow fibers each fiber having an outer wall surface, an inner wall surface and an interior lumen extending along the length thereof, said fiber wall having an asymmetrical pore size and asymmetrical mass density morphology between inner and outer fiber walls wherein the mass density adjacent to said outer wall is greater than the mass density adjacent to said inner wall;

separating blood plasma and disease-related components therein from whole blood in-vivo by passing said plasma through the wall of said fibers from the outer wall to the inner wall and through a first lumen of said triple lumen catheter to a therapeutic apheresis selective component removal apparatus;

carrying out therapeutic apheresis by separating and removing and/or neutralizing selected disease-related components comprising toxins, antibodies, proteins, bacteria, viruses, and/or combinations of two or more thereof from the plasma; and returning treated plasma to the patient via a second lumen of said triple lumen catheter.

13. A method of claim 12 wherein the fiber wall structure is a continuous change in mass density from said outer wall to said inner wall and comprises a continuum of voids bounded by solid frames.

14. A method of claim 12 wherein said fiber wall comprises a plurality of zones between inner and outer wall surfaces, each of said zones having a mass density different than the mass density of an adjacent zone.

15. The method of claim 12, 13 or 14 including selectively periodically backflushing said filter device via a third lumen of said triple lumen catheter.

16. The method of claim 12, 13 or 14 wherein said therapeutic apheresis is carried out by plasma exchange wherein at least a portion of the separated plasma is replaced with fresh plasma.

17. The method of claim 12, 13 or 14 wherein said therapeutic apheresis is carried out by cascade filtration.

18. The method of claim 3 including substituting fresh plasma for a portion of said separated plasma.

19. The method of claim 12, 13 or 14 wherein said therapeutic apheresis is carried out by absorption.

20. The method of claim 19 comprising passing the separated plasma through an absorbent cartridge apparatus for absorbing disease-related components therefrom.

21. The method of claim 19 including substituting fresh plasma for a portion of said separated plasma.

22. The method of claim 12, 13 or 14 wherein said therapeutic apheresis is carried out by exposing the separated plasma to one or more devices capable of removing a specific disease-related component from the separated plasma.

23. The method of claim 22 including substituting fresh plasma for a portion of said separated plasma.

24. The method of claim 12, 13 or 14 wherein said therapeutic apheresis is carried out by directing the separated plasma through one or more chemical process systems for precipitating or neutralizing one or more disease-related components therein.

25. The method of claim 24 including substituting fresh plasma for a portion of said separated plasma.

* * * * *